United States Patent [19]

Schweikhart

[11] Patent Number: 4,597,763
[45] Date of Patent: Jul. 1, 1986

[54] IMPLANTABLE MOLDED PLASTIC PART

[75] Inventor: Gertfried Schweikhart, Ober-Olm, Fed. Rep. of Germany

[73] Assignee: Rohm GmbH Chemische Fabrik, Darmstadt, Fed. Rep. of Germany

[21] Appl. No.: 589,538

[22] Filed: Mar. 14, 1984

[30] Foreign Application Priority Data

Mar. 18, 1983 [DE] Fed. Rep. of Germany ... 8308005[U]

[51] Int. Cl.⁴ .............................................. A61F 1/00
[52] U.S. Cl. ...................................................... 623/8
[58] Field of Search .............. 3/1, 36, 13 A; 128/456, 128/463, 464, 481, 499; D24/33, 64

[56] References Cited

U.S. PATENT DOCUMENTS

| D. 277,606 | 2/1985 | Cebula | D24/33 |
|---|---|---|---|
| 2,664,571 | 1/1954 | Kempel | 128/481 |
| 2,834,023 | 5/1958 | Lieb | 3/13 A |
| 3,947,207 | 3/1976 | Magidson et al. | 3/36 |
| 3,986,213 | 10/1976 | Lynch | 3/36 |
| 4,258,442 | 3/1981 | Eberl | 3/36 |
| 4,264,990 | 5/1981 | Hamas | 3/36 |

FOREIGN PATENT DOCUMENTS 0005275  11/1979  European Pat. Off. ................ 3/36

Primary Examiner—Richard J. Apley
Assistant Examiner—David J. Isabella
Attorney, Agent, or Firm—Oblon, Fisher, Spivak, McClelland & Maier

[57] ABSTRACT

A lenticular, rigid, optionally hollow, molded plastic part wet-resistant toward aqueous media, for example acryl glass, is proposed as an implantable temporary filler for a mammary gland prosthesis that can be implanted in surgery following amputation of the mammary gland until after the healing of the site of the operation. The molded part has an oval horizontal projection and is bounded by two curved surfaces, one of them a concave and an approximately cylindrical surface whose curvature is adapted to the human thorax in the area of the breast and the other an approximately spherical surface whose radius is smaller than the radius of curvature of the cylindrical surface.

8 Claims, 4 Drawing Figures

IMPLANTABLE MOLDED PLASTIC PART

BACKGROUND OF THE INVENTION

1. Field of Invention

This invention relates to a lenticular plastic part that is used in surgery as temporary filler for a breast prosthesis following amputation of the mammary gland, especially in breast cancer surgery.

2. Description of the Prior Art

Following amputation of the mammary gland it is now the widely accepted practice to implant in the resulting skin pocket a prosthesis consisting of silicone gel that is enclosed in a plastic film. A spherical deformation of the prosthesis frequently occurs because of the scarring process, the so-called capsule fibrosis. To remedy this defect, Gianella ("Cancer of the Breast and Breast Reconstruction"; Internat. Symposium, Munich, Publisher: Heinz Bohmert, Georg Thieme Publishing Company, Stuttgart-New York, 1982, pages 183–187) and Audretsch (loc. cit, pages 92–100) proposed first implanting a temporary filler following the amputation and then replacing it with the final prosthesis in a second operation following complete healing of the site of the operation.

Gianella uses as a temporary filler a liquid-filled plastic film whose volume can be modified in the implanted state. Audretsch implants as a temporary filler a flat circular disk made of flexible silicone material. Neither type of temporary filler sufficiently prevents the development of heavy scar tissue from which the disturbing capsule fibrosis may develop later on. Furthermore, the possibility of shrinking of the skin and a joining of the inner wound surface with the plastic cannot be excluded.

SUMMARY OF THE INVENTION

The invention is based on the problem of developing an implantable molded part to be used as a temporary filler that does not have the described disadvantages of the known temporary filler or has them to a reduced degree.

Thus, in accordance with the present invention, the above problem has been solved by an implantable, lenticular, rigid, optionally hollow molded part comprising a wet-resistant plastic that is bounded by two curved surfaces and an oval horizontal projection with one of the curved surfaces being a concave approximately cylindrical surface whose curvature is adapted to the human thorax in the breast area and the other surface being an approximately spherical surface whose radius is smaller than the radius of curvature of the cylindrical surface.

These and other aspects of the invention will become clear to those skilled in the art upon the reading and understanding of the specification.

Figure 1:
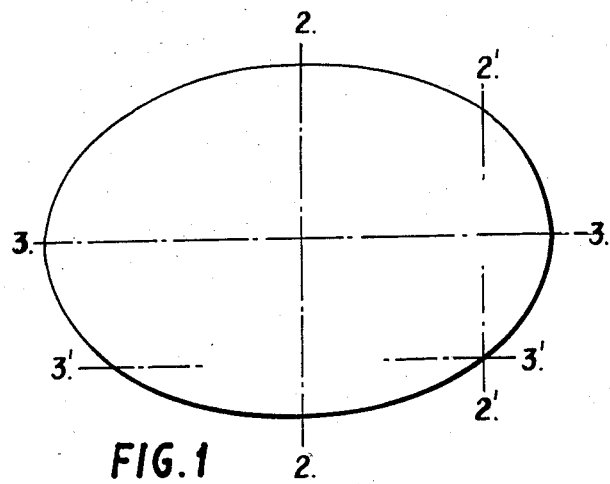
FIG. 1 shows the horizontal projection of the molded part.
Figure 2:
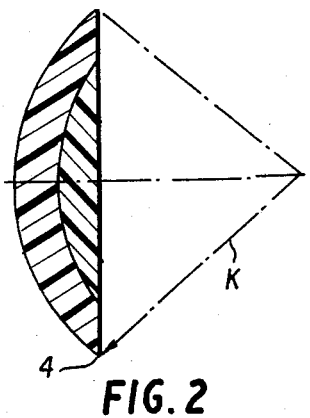
FIGS. 2 and 3 show, with hatching, the intersecting planes along lines 2—2 or 3—3 in FIG. 1.
Figure 3:
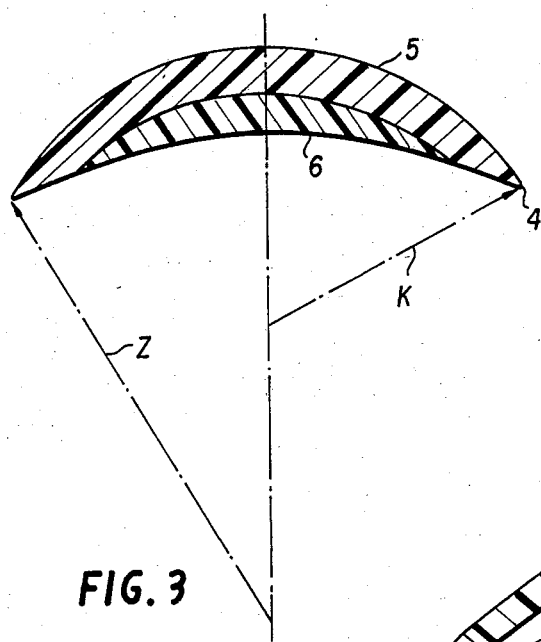

Further intersecting planes along lines 2'—2' or 3'—3' are shown, with crosshatching, in FIGS. 2 and 3.

Figure 4:
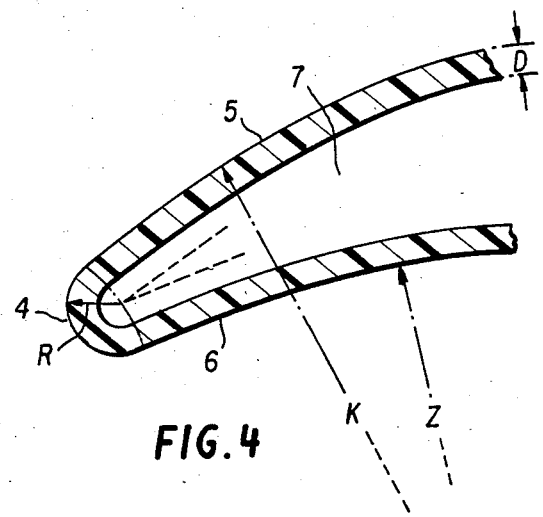

FIG. 4 shows a cross section through a preferred embodiment of the invention in a manner of presentation corresponding to FIG. 3.

DETAILED DESCRIPTION OF THE PREFERRED EMBODIMENTS

Of considerable importance for the characteristics of the implantable molded part is the plastic used and its surface properties. Histological evidence indicates that the formation of extensive scar tissue during healing of the site of the operation is suppressed if the plastic is wet-resistant toward aqueous media. Since roughness promotes wettability, the plastic surface should be as smooth and nonporous as possible. Furthermore, the material should not swell or soften in an aqueous environment. The water absorption should remain within such limits that the wettability is not significantly affected and the mechanical characteristics remain largely unchanged.

The wettability of a plastic can be tested by measurement of the contact angle of a drop of water lying thereon, according to DIN (German industrial standard) 53900. The plastics suitable for the invention have contact angles of at least 50°, particularly 60°–75°.

The molded part overall is rigid or stable in shape, i.e., it will not be visibly deformed in any position under its own weight. With the effect of the forces that normally can also affect the human body without harm, the molded part may elastically deform, especially the radius of curvature of the cylindrical surface may change; however, such deformations must disappear again when the deforming force slackens.

The plastic must be tissue-compatible in every respect and must not generate any toxic components. Plastics of this type of are known. They include acryl glass, by which are meant especially the methylmethacrylate polymers and the copolymers from a preponderant part of this ester with other comonomers, especially with esters of acrylic acid or higher esters of methacrylic acid. In the interest of higher flexibility, consideration is to be given to acrylic plastics made of a preponderant share of acrylic and higher methacrylic esters, optionally together with homopolar or heteropolar crosslinking monomers. Acryl glass stands out among plastics by its extraordinary tissue compatibility.

No less than the nature of the plastic, the shape of the molded part is of importance for the effect to be achieved. This effect is solely concerned with guaranteeing undisturbed healing of the site of the operation. In addition to the especially low-irritating plastic surface, it is important that the wound tissue is kept immobile in its original natural position by means of the rigid molded part. The shape of the molded part is adapted to the amputated mammary gland, so that no hollow spaces remain in the area of the wound that the organism could fill with excess scar tissue during the healing process. After healing of the wound, the temporary filler can be removed and replaced by the permanent prosthesis made of a film-encapsulated silicone gel following a skin incision that causes only an infinitesimal wound site compared to the preceding amputation operation. This prosthesis takes up the same space as the previously implanted temporary filler and thus does not cause any new changes. During the healing of the internal wound surfaces, an irritation-free, smooth hollow space develops adapted to the shape of the temporary filler, a hollow space that corresponds to the former mammary gland.

The shape of the molded part corresponds to the natural shape of the breast with the patient in supine position. The description in claim 1 as a molded part bounded by a spherical surface and a cylindrical surface serves the purpose of objective characterization of the shape of the molded part. The purpose explained in detail above, does not require a precise adherence to these geometric forms but permits divergences as long as they do not run counter to the medical purpose. Therefore, the above-mentioned surfaces need only approximately correspond to a spherical or cylindrical surface.

The radius Z of the cylindrical surface corresponds to the radius of curvature of the thorax in the area of the breast, including the muscle system lying over the ribs. It is advisable to determine the radius Z individually according to the thorax of the patient to be treated and to take into consideration any possible divergences from the circular cylindrical shape.

The radius K of the spherical surface, too, is preferably adapted to the patient's measurements.

The intersecting line of the spherical surface (5) with the cylindrical surface (6) represents a sharp edge in the geometrical sense that would cause tissue irritation in the implanted state and thus would be inappropriate. Therefore, the spherical surface (5) can advantageously connect with the cylindrical surface (6) through a curved region whose radius of curvature R is from about 0.5 to 5 mm.

According to a preferred embodiment, the molded part, according to FIG. 4, is shaped as a hollow body with at least one hollow space (7) and a wall thickness D of the plastic shell from about 1 to 5 mm. This simplifies not only the production for which flat acryl glass of about thickness D can be used but also the molded part can have a considerably lower weight than a solid body. The weight can be less than 200 g, preferably less than 100 g. In a typical case, the weight is 50 g and the wall thickness 1.5 mm.

Appropriately for the production of the molded part, the spherical surface (5) and the cylindrical surface (6) are formed in each case from a planar plastic sheet material in a manner known in the art. Then the cuts are bonded to corresponding oval bases by means of a suitable cementing technique and the edges are rounded and polished. It is advantageous to drill a small hole into one of the initial surfaces to be able to remove gaseous components of the adhesive that might possibly have gotten into the hollow space. Then the drill hole is closed.

What is claimed as new and desired to be secured by Letters Patent of the United States is:

1. A molded part for use in surgery as a temporary filler for the breast prosthesis, comprising a wet-resistant plastic that is bounded by two curved surfaces and an oval horizontal projection with one of the curved surfaces being a concave approximately cylindrical surface whose curvature is adapted to the human thorax in the breast area and the other surface being an approximately spherical surface whose radius is smaller than the radius of curvature of the cylindrical surface, said molded part consisting of acryl glass, being rigid overall, and having a smooth and non-porous surface.

2. The molded part as in claim 1 wherein the cylindrical surface and the spherical surface connect with each other through a curved region whose radius of curvature is between 0.5 and 5 mm.

3. The molded part as in claim 1, wherein the spherical surface has a radius of from 4 to 10 cm and the cylindrical surface a radius of curvature of from 8 to 20 cm.

4. The molded part as in claim 1, wherein the volume of said molded part is from 100 to 300 $cm^3$.

5. The molded part as in claim 1, wherein said molded part is made of a wet-resistant plastic possessing a contact angle with water of at least 50°.

6. The molded part as in claim 1, wherein said molded part is made of a wet-resistant plastic possessing a contact angle with water of between 60° and 75°.

7. The molded part as in claim 1, wherein said molded part contains at least one hollow space in the interior of said molded part.

8. The molded part as in claim 1, wherein the spherical surface has a radius of from 4 to 10 cm and the cylindrical surface a radius of from 8 to 20 cm, wherein the spherical surface and the cylindrical surface connect with each other through a curved region whose radius of curvature is between 0.5 and 5 mm, wherein said part is made of a wet-resistant plastic possessing a contact angle with water of between 60° and 75°, wherein said part has a volume of from 100 to 300 $cm^3$ and wherein said part contains at least one hollow space in the interior of said part.

* * * * *